(12) United States Patent
Bengtsson et al.

(10) Patent No.: US 8,187,462 B2
(45) Date of Patent: May 29, 2012

(54) PROCESS FOR MAXIMIZING PHA PRODUCTION IN GLYCOGEN ACCUMULATING ORGANISMS

(75) Inventors: Simon Olof Harald Bengtsson, Lund (SE); Alan Gideon Werker, Lomma (SE); Paulo Alexandre da Costa Lemos, Belas (PT); Maria Ascensao Carvalho Fernandes de Miranda Reis, Lisboa (PT)

(73) Assignee: OTV SA, Saint-Maurice Cedex (FR)

( * ) Notice: Subject to any disclaimer, the term of this patent is extended or adjusted under 35 U.S.C. 154(b) by 335 days.

(21) Appl. No.: 12/704,732

(22) Filed: Feb. 12, 2010

(65) Prior Publication Data

US 2010/0200498 A1    Aug. 12, 2010

Related U.S. Application Data

(60) Provisional application No. 61/151,940, filed on Feb. 12, 2009.

(51) Int. Cl.
*C02F 3/30* (2006.01)

(52) U.S. Cl. .................... 210/605; 435/262.5

(58) Field of Classification Search .......... 210/605, 210/612, 613, 630; 435/262, 262.5
See application file for complete search history.

(56) References Cited

U.S. PATENT DOCUMENTS 6,991,931 B2 * 1/2006 Dragotta et al. ............. 435/262

OTHER PUBLICATIONS

Bengtsson et al., "Production of polyhydroxyalkanoates by glocogen accumulating organisms treating a paper mill wastewater", Water Science & Technology, IWA Publishing, 2008, (XP-002604619).

Bengtsson et al., "Production of Polyhydroxyalkanoates by Activated Sludge Treating a Paper Mill Wastewater"; ScienceDirect, Bioresource Technology 99 (2008) 509-516.

Albuquerque et al., "Strategies for the development of a side stream process for polyhydroxyalkanoate (PHA) production from sugar cane molasses"; ScienceDirect, Journal of Biotechnology 130 (2007) 411-421.

Dai et al., "Anaerobic metabolism of Defluviicoccus vanus related glycogen accumulating organisms (GAOs) with acetate and propionate as carbon sources"; ScienceDirect, journal homepage: www.elsevier.com/locate/watres, Water Research 41 (2007) 1885-1896.

(Continued)

*Primary Examiner* — Fred Prince
(74) *Attorney, Agent, or Firm* — Coats & Bennet, P.L.L.C.

(57) ABSTRACT

A process is provided for increasing the production of PHA in a mixed culture biomass. In a first stage of the process, organic material associated with a substrate is converted to volatile fatty acids. In the case of a wastewater treatment process, if the wastewater includes sufficient volatile fatty acids (VFAs) to support the process, then it is unnecessary to convert organic material to VFAs. In a second stage of the process, an anaerobic-aerobic selection process is utilized to select glycogen accumulating organisms that cause these organisms to proliferate and dominate the open mixed culture biomass. By providing relatively high organic loading in the form of VFAs in the anaerobic treatment phase of the selection process, glycogen accumulating organisms having a relatively high level of stored glycogen are produced. In a third stage, the PHA accumulation process is practiced where the glycogen rich organisms are fed VFAs under anaerobic or aerobic conditions or combinations thereof. Through the consumption of externally supplied VFAs and internally stored glycogen, relatively high levels of PHA in the biomass are produced. Thereafter PHA is separated from the residual biomass.

30 Claims, 5 Drawing Sheets

OTHER PUBLICATIONS

Serafim, et al., "Strategies for PHA production by mixed cultures and renewable waste materials", App. Microbiol Biotechnol (2008) 81:615-628.

Zeng et al., "Metabolic Model for Glycogen-Accumulating Organisms in Anaerobic/Aerobic Activated Sludge Systems", 2002 Wiley Periodicals, Inc., (XP-002604504).

Bengstsson, Simon; "The Utilization of Glycogen Accumulating Organisms for Mixed Culture Production of Polyhydroxyalkanoates"; Biotechnology and Bioengineering, vol. 104, No. 4, Nov. 1, 2009 (XP-002604505).

Beccari, et al., "Exploiting olive oil mill effluents as a renewable resource for production of biodegradable polymers through a combined anaerobic-aerobic process", J Chem Technol Biotechnol 2009, 84:901-908 (XP-002604620).

* cited by examiner

Figure 1. Concentrations of acetate (×), 3HB (♦), 3HV (▼), glycogen (○), active biomass (□) and orthophosphate (△).

Figure 2. Concentrations of acetate (×), 3HB (♦), 3HV (▼) and glycogen (○).

FIGURE 2

Figure 3. Concentrations of acetate (×), oxygen uptake rate (■), 3HB (♦), 3HV (▼) and glycogen (o).

FIGURE 3

Figure 4. Concentrations of acetate (×), oxygen uptake rate (■), 3HB (♦), 3HV (▼) and glycogen (○).

PROCESS FOR MAXIMIZING PHA PRODUCTION IN GLYCOGEN ACCUMULATING ORGANISMS

CROSS-REFERENCE TO PROVISIONAL APPLICATION

This application claims priority under 35 U.S.C. §119(e) from the following U.S. provisional application: Application Ser. No. 61/151,940 filed on Feb. 12, 2009. That application is incorporated in its entirety by reference herein.

BACKGROUND OF THE INVENTION

Polyhydroxyalkanoates (PHAs) have been considered promising candidates as environmentally friendly polymer materials. These polymers exhibit a broad range of material properties and can be produced from renewable resources. However, high production costs associated with traditional PHA production carried out with pure microbial cultures have limited broad application of these polymers. Alternative PHA production strategies have been proposed based on the use of mixed cultures. The use of mixed cultures for PHA production may be more cost effective since it does not require sterile conditions. In addition, it allows for the use of inexpensive substrates such as wastes or waste by-products.

SUMMARY

The present invention relates to a process for increasing the production of PHA in a mixed culture biomass. In a first stage of the process, organic material associated with the substrate is converted to volatile fatty acids (VFAs). In a second stage, an anaerobic-aerobic selection process is utilized to select glycogen accumulating organisms (GAOs) and cause GAOs to proliferate and dominate the open mixed-culture biomass. By providing relatively high organic loading in the form of VFAs in the anaerobic phase of the selection process, GAOs having a relatively high level of stored glycogen are produced. In stage three, a PHA accumulation process is practiced where the glycogen rich GAO biomass is fed VFAs under anaerobic or aerobic conditions or combinations thereof. Through the consumption of the externally supplied VFA rich substrate and the internally stored glycogen, relatively high levels of PHA in the biomass are produced. Thereafter, the PHA is separated from the residual biomass.

In some processes, all three stages may not be necessary. For example, the substrate may already be sufficiently rich in VFAs to warrant unnecessary the organic conversion step before proceeding with GAO selection. Furthermore, in some cases it may be feasible to integrate the PHA accumulation process into the stage two GAO selection process.

More particularly, the process of the present invention relates to producing PHAs by an open mixed culture of selected or enriched GAOs where during the anaerobic phase of the selection process relatively high loading ratios of VFA to biomass is maintained. This has been found to give rise to a relatively high level of intracellular glycogen, which in turn facilitates a mechanism that provides for the accumulation of relatively high amounts of PHA. While the VFA loading during the anaerobic phase of the selection process can vary, it has been discovered that VFA to biomass (dry weight) loading ratios in the range of 0.075 to 0.126 g-VFA/g-biomass is effective to produce a biomass that comprises approximately 17% to approximately 60% PHA. This range of ratios is not limiting. It is postulated, through experimental tests, that higher ratios exceeding 0.126 g-VFA/g-biomass are also effective in producing substantial amounts of glycogen, which in turn results in the production of a substantial amount of PHA.

DESCRIPTION OF EXEMPLARY EMBODIMENTS

Polyhydroxyalkanotes (PHAs) are a group of biopolymers synthesized in bacteria as intracellular carbon and energy reserves. One group of organisms found in biomass, termed glycogen accumulating organisms (GAOs), produce PHAs under certain conditions. GAOs metabolize external sources of carbon, usually volatile fatty acids (VFAs) and store the carbon in the form of PHAs.

The present invention involves increasing PHA production in mixed cultures enriched in GAOs. The process described herein may include at least three stages. In the first stage, organic matter comprising the substrate is converted into volatile fatty acids (VFAs). The second stage is a GAO selection process that uses alternating anaerobic-aerobic conditions and consumes the VFAs during the anaerobic period. Although VFAs are generally viewed as preferred substrates for GAOs, other types of organic compounds may also serve as substrates. In this stage the GAOs grow and proliferate, and come to dominate the biomass if a phosphorus source is not provided in excess of growth requirements. In the third stage, the PHA in the GAOs is produced and accumulated to as high extent as possible. The object of the present invention is to produce high amounts of PHA as this will improve overall process production performance and will substantially improve downstream processing, making it easier and more cost effective to separate PHA from residual biomass. The process described herein becomes increasingly more economically and technically feasible the higher the PHA level achieved in the accumulation stage.

As mentioned above, the first stage of the process involves converting organic matter into VFAs. This is accomplished by providing a carbon substrate to a fermentation biomass under anaerobic conditions in a process often referred to as acidogenesis. Carbon sources may vary but the resulting VFAs can include mixtures of acetate, propionate, butyric, and valerate. However, in some circumstances, the substrate to be used to enrich for GAOs may already have a sufficient VFA content, or for various reasons it may not be practical or feasible to convert organic matter to increase VFA content. In these circumstances, the first stage of the process may not be necessary. In either scenario, the substrate containing VFAs is fed to the GAO biomass in the second stage during an anaerobic phase and, in so doing, driving and maintaining a stable GAO selection pressure.

The GAO selection process may be carried out in the second stage, which in one embodiment may be a sequencing batch reactor (SBR). However, in other embodiments, GAO selection may be similarly achieved in plug flow reactors, a series of mixed tanks, or other continuous flow reactor configurations. During the anaerobic period of the GAO selection process, VFAs are fed to the GAOs. The GAOs hydrolyze and consume intracellularly stored glycogen and the energy produced during these reactions is used to consume the VFAs to produce and store PHA. Under anaerobic conditions, no oxygen is supplied to the biomass and the dissolved oxygen level in the mixed liquor is non-existent or at least relatively low. During the following aerobic period of the GAO selection process, the VFA supply is no longer available and thus, the internally stored PHA is used for growth of active biomass and the production of intracellular glycogen. This process selectively enriches a biomass with GAOs since GAOs can thrive under such anaerobic-aerobic conditions while many other non-glycogen accumulating organisms cannot survive under such conditions. Under aerobic conditions, oxygen or another electron acceptor is available to the biomass facilitating PHA consumption as a carbon source for cellular grown and glycogen storage. Oxygen can be supplied using for example, aerators or mixers. In another embodiment, the GAO selection phase can include an anoxic phase used in conjunction with the aerobic phase. In yet another embodiment, the GAO selection process may comprise anaerobic-anoxic conditions. When employing an anoxic phase, $NO_3^-$ (nitrate) or $NO_2$ (nitrate) can be used as suitable anoxic electron acceptors.

In the third stage, PHA in the GAOs is produced and accumulated to as high a level as possible. If the biomass is harvested from the GAO selector during the anaerobic period, the GAOs have high levels of stored PHA resulting from the metabolized VFAs. Thus, the biomass may not require further treatment if harvested after the anaerobic phase. However, if the biomass is harvested from the GAO selector during the aerobic period, the GAOs have oxidized a significant amount of the stored PHA into glycogen. Accordingly, if the biomass is harvested during the aerobic period during the GAO selection process and has little or no stored PHA, additional treatment is necessary to produce and accumulate PHA. VFAs can be added to this type of biomass to stimulate PHA production under either anaerobic conditions or aerobic conditions alone or in combination.

By controlling various parameters of the GAO selection phase described above, the accumulation of PHAs in GAOs can be increased. For example, if the glycogen content in the harvested GAOs is sufficiently high, then added VFAs during the accumulation stage are consumed with concomitant consumption of glycogen and PHA production. GAOs depend on glycogen for PHA synthesis under anaerobic and aerobic conditions. Accordingly, ensuring high glycogen content in the GAOs during the GAO selection phase enables increased PHA production potential during accumulation by either anaerobic or aerobic strategies.

Several parameters contribute to maximizing glycogen content in the GAOs during the GAO selection phase. One parameter used to maximize glycogen content is a VFA to biomass weight ratio. In continuous flow systems this parameter is often referred to as "floc-loading". The amount of VFA is defined by the sum total of all the individual volatile fatty acids present in the substrate. One way to represent the amount of biomass being fed is through the measurement of total suspended solids (TSS). For SBRs, the VFA to biomass ratio can be defined as the mass of VFA fed to the biomass during the anaerobic phase divided by the biomass measured as TSS in the start of the anaerobic phase (g VFA/g TSS). For continuously flow with simple or distributed feed reactor configurations, the VFA to biomass ratio can be defined as the rate of VFA supplied to the anaerobic zone (g VFA/h) divided by the rate of biomass supplied to the anaerobic zone (g TSS/h). Controlling this parameter increases the glycogen levels in a GAO biomass in order to subsequently maximize the PHA accumulation potential in the biomass. As discussed below, VFA to TSS ratios in the range of 0.075 to 0.126 g-VFA/g-TSS proves to yield high intracellular levels of glycogen which enable high levels of PHA to accumulate. Generally, the VFA to biomass ratio should be 0.08 g VFA/g TSS or above.

High organic loading during the anaerobic phase of the GAO selection process is important in producing GAOs having high levels of intracellular glycogen, which in turn results in high PHA production during subsequent PHA accumulation under anaerobic and/or aerobic conditions. A number of experiments where the VFA to TSS ratio ranged from 0.075 to 0.126 were conducted and established that high ratios of VFAs to TSS result in high accumulation of PHA.

In one example, the GAO selection process was achieved using an SBR with a VFA to biomass ratio of 0.075 g VFA/g TSS. The GAOs contained 18% glycogen of the total suspended solids at the end of the aerobic phase. When feeding excess VFAs to this biomass in the PHA accumulation phase, 17% PHA of the resultant TSS was obtained under anaerobic conditions.

In another example, the GAO selection process was achieved using an SBR with a VFA to biomass ratio of 0.084 g VFA/g TSS. The GAOs contained 24% glycogen of the total suspended solids at the end of the aerobic phase. When feeding excess VFAs to this biomass in the PHA accumulation phase, 30% PHA of the resultant TSS was obtained under anaerobic conditions and 25% PHA of the resultant TSS under aerobic conditions.

In yet another example, the GAO selection process was achieved using an SBR with a VFA to biomass ratio of 0.126 g VFA/g TSS. The GAOs contained 36% glycogen of the total suspended solids at the end of the aerobic phase. When feeding excess VFAs to this biomass in the PHA accumulation phase, 49% of the resultant TSS was in the form of PHA under anaerobic conditions and 60% of the resultant TSS was in the form of PHA under aerobic conditions.

For a more detailed explanation of the GAO selection process and PHA accumulation, see Exhibit 1.

Other parameters that contribute to maximizing intracellular glycogen content during the GAO selection phase include temperature and the solids retention time (SRT). Notwithstanding, the strategy for the GAO selection process can be operated over a wide range of temperatures and SRTs.

Of key consequence is the design of length of the alternating anaerobic and aerobic periods that biomass is exposed to in the GAO selection process. The anaerobic phase of the GAO selection process should be long enough to allow for VFA consumption but short enough to avoid undue anaerobic consumption of stored PHA. A typical range of the anaerobic phase time is between one and four hours. The time during the aerobic period of the GAO selection phase should be sufficient to reduce intracellular PHA concentration but short enough to avoid undue consumption of stored glycogen. Generally, the aerobic time is long enough such that the stored PHA content becomes less than 10% of the biomass measured as TSS. A typical range of time for the aerobic phase is between two and twenty hours.

Figure 1:
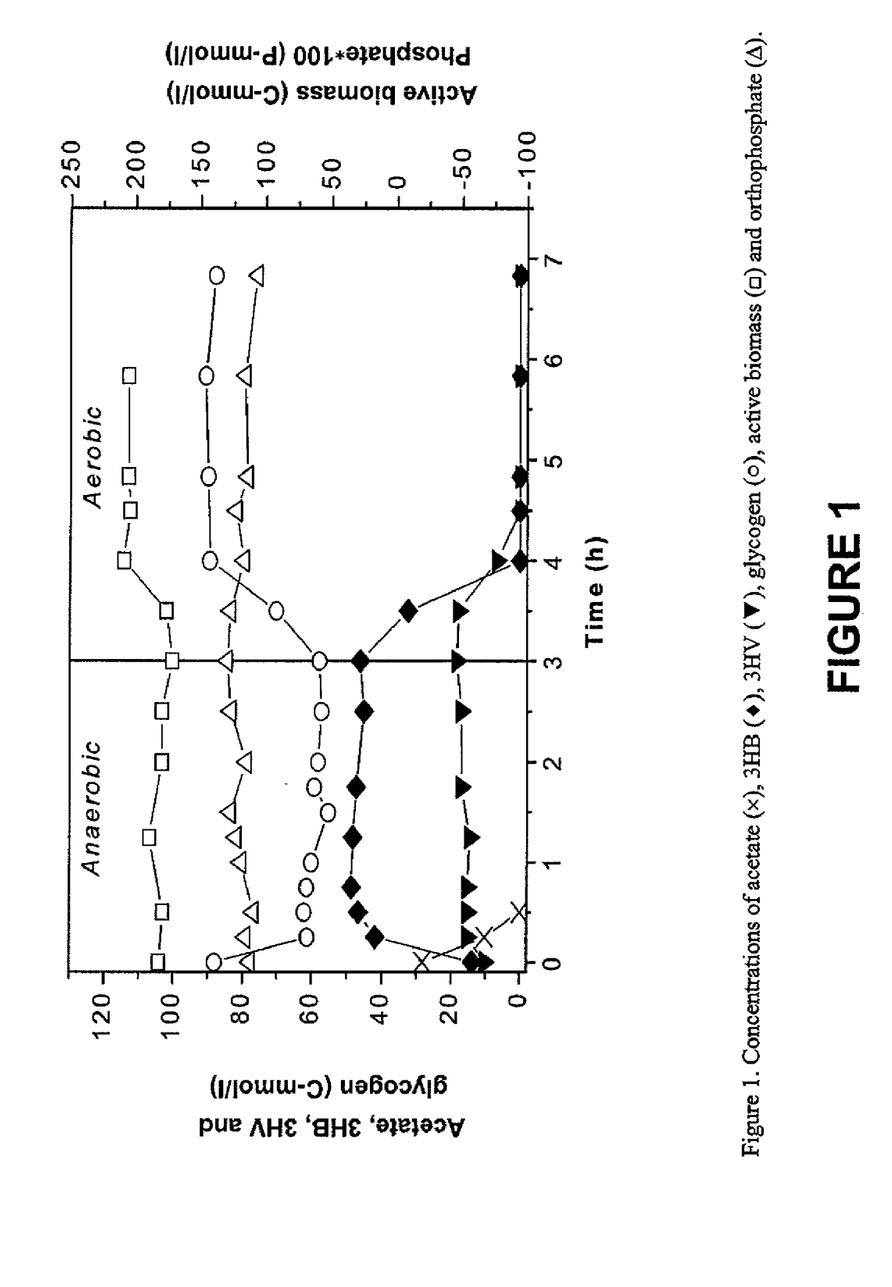
FIG. 1 is a chart illustrating a typical anaerobic-aerobic cycle in a GAO selection process.

In one example, the GAO selection process was carried out using an SBR fed with acetate as the VFA source and operated under alternating anaerobic-aerobic conditions for 450 days at approximately 30° C. During this period, *Candidatus* Competibacter phosphatis dominated the culture at between 54% and 70% of the biomass. A typical anaerobic-aerobic cycle is depicted in FIG. 1. As shown in FIG. 1, during the anaerobic phase of the GAO selection process, acetate and glycogen were consumed and PHA was simultaneously produced. During the subsequent aerobic phase, PHA was consumed and active biomass and glycogen were produced.

The GAO selection process was achieved with a VFA to biomass ratio of 0.126 g VFA/g TSS. At the end of the anaerobic phase, the PHA content was 17±3 of TSS and glycogen content was 17±2% of TSS. At the end of the aerobic phase, the glycogen content was 36±4% of TSS. A high VFA to biomass ratio in the GAO selection process promotes enhanced glycogen content in GAOs by the end of the aerobic phase.

Accumulation of PHA under anaerobic and aerobic conditions was studied in separate batch experiments. Accordingly, biomass from the SBR was removed at the end of the aerobic phase and transferred to a batch reactor. A VFA source, such as acetate or propionate, was added to the biomass in single or multiple pulses of 1 or 2 g acetate or propionate per L. Accumulation of PHA under aerobic or anaerobic conditions proceeded so long as glycogen was present in the GAO biomass. PHA is produced with the simultaneous consumption of externally supplied VFA and internally stored glycogen.

Figure 2:
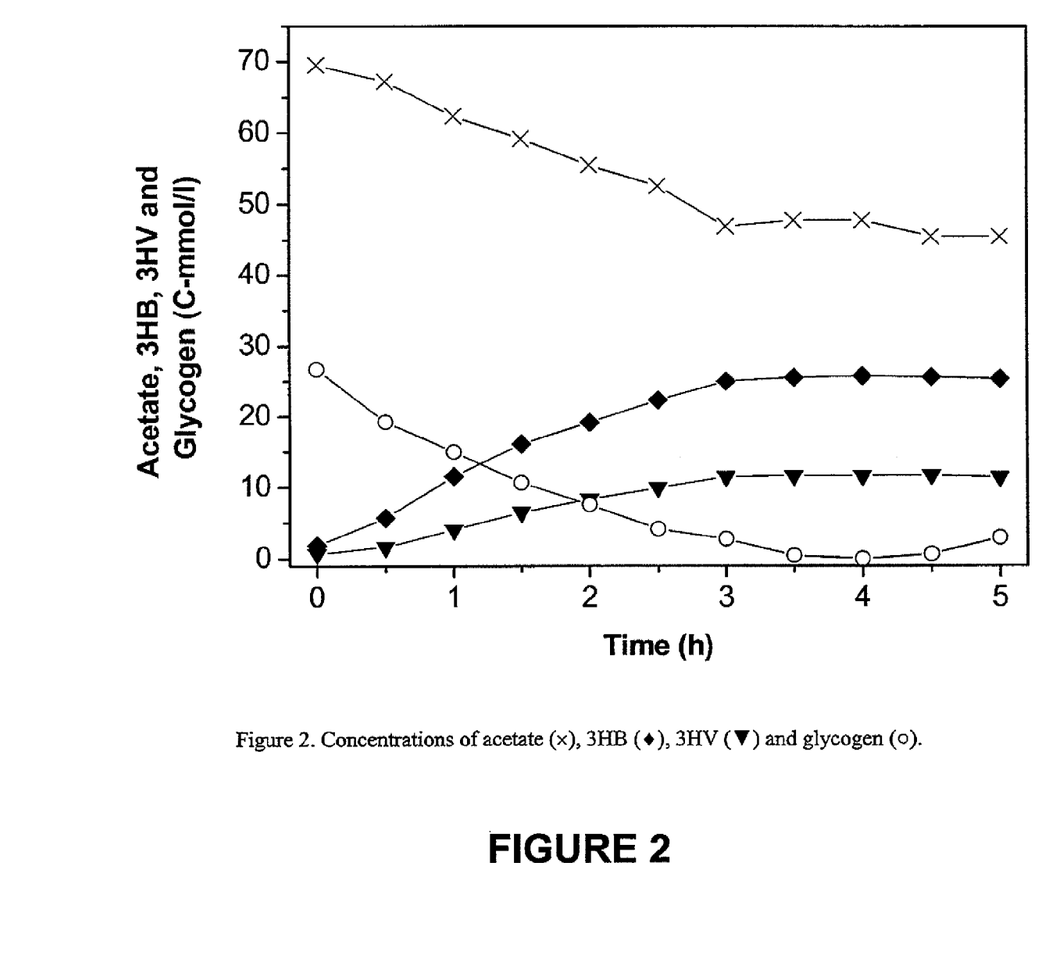
FIG. 2 is a chart illustrating an anaerobic PHA accumulation process.

When feeding excess VFAs to the biomass in the PHA accumulation phase, 49% of the resultant biomass measured as TSS was in the form of PHA and was obtained within four hours under anaerobic conditions. The accumulated PHA contained both 3-hydroxybutyrate (3HB) and 3-hydroxyvalerate (3HV). As shown in FIG. 2, accumulation of PHA ceased when the intracellular glycogen content fell below 3% of TSS, indicating that PHA accumulation was limited by the amount of glycogen stored.

Figure 3:
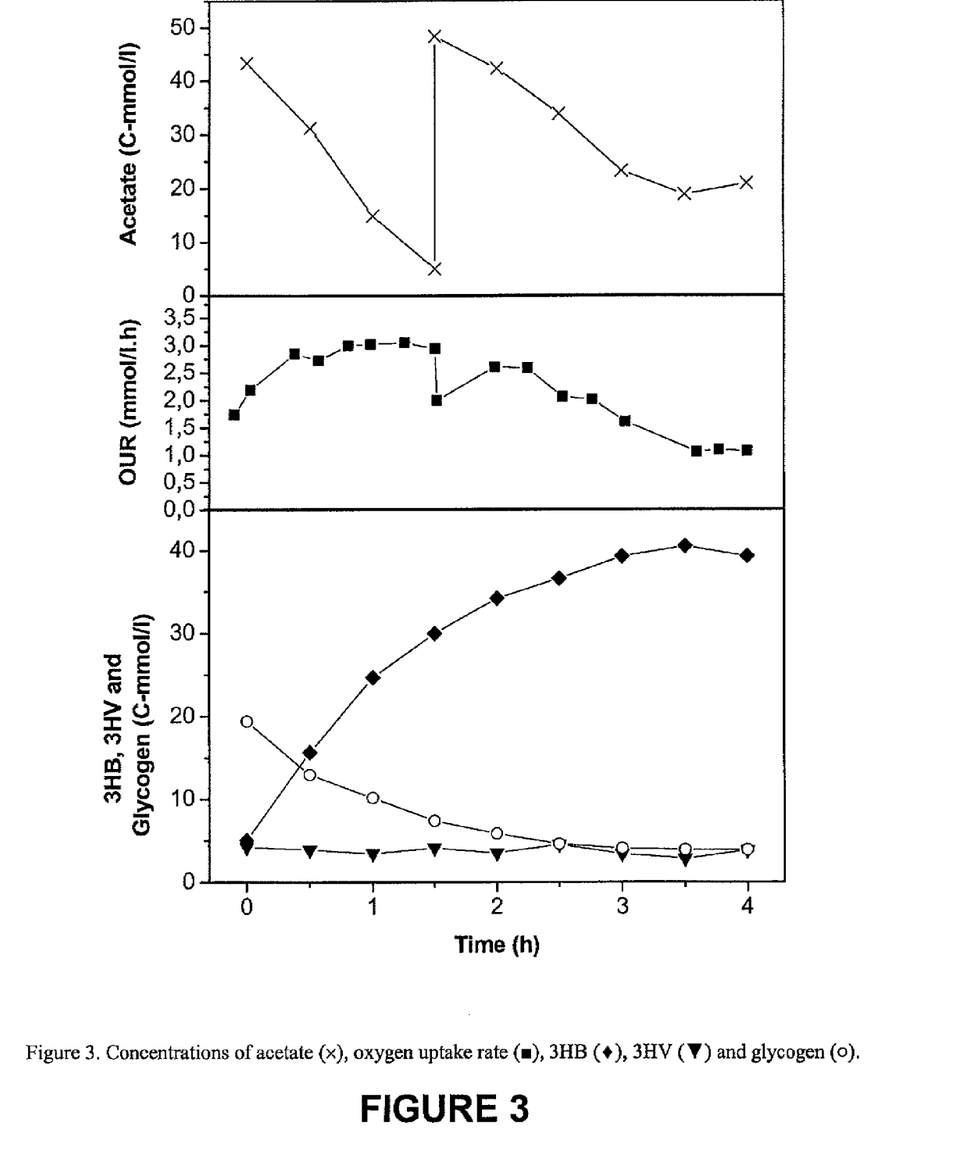
FIG. 3 is a chart illustrating an aerobic PHA accumulation process where two pulses of 50 C-mmol/L acetate were added to the biomass.
Figure 4:
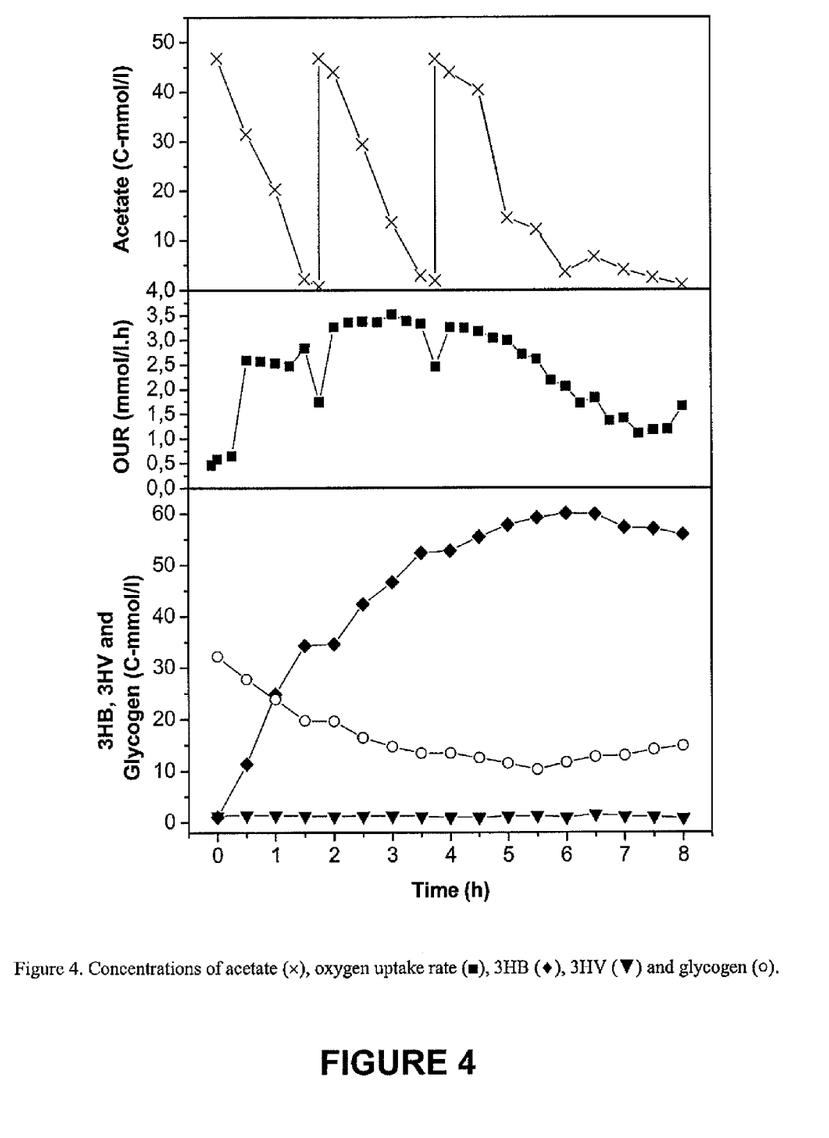
FIG. 4 is a chart illustrating an aerobic PHA accumulation process where three pulses of 50 C-mmol/L acetate were added to the biomass.

During the PHA accumulation phase in aerobic conditions, two pulses of 50 C-mmol/L acetate were added to the biomass. Under these conditions, 60% of the resultant biomass measured as TSS was in the form of PHA. In a separate experiment under aerobic conditions, three pulses of 50 C-mmol/L acetate were added to the biomass. Under these conditions, 59% of the resultant biomass measured as TSS was in the form of PHA. In both aerobic accumulation experiments, the accumulated PHA contained only 3HB. In addition, FIGS. 3 and 4 show that in both aerobic accumulation experiments, the PHA production rate and the glycogen consumption rate decreased over time, as was observed under anaerobic conditions. Accordingly, intracellular glycogen levels control the PHA production under aerobic conditions as well as under anaerobic conditions.

One experiment was conducted under 4 h anaerobic followed by 4 h aerobic conditions with acetate supplied in pulses. When the glycogen pool was exhausted (3% of TSS) due to anaerobic PHA accumulation, no further PHA accumulation under aerobic conditions occurred even though the biomass was not saturated with PHA as evident from a PHA content (47% of TSS) lower than the highest PHA content observed for the culture (60% of TSS). This shows that PHA synthesis in GAOs is dependent on glycogen consumption also under aerobic conditions.

Figure 5:
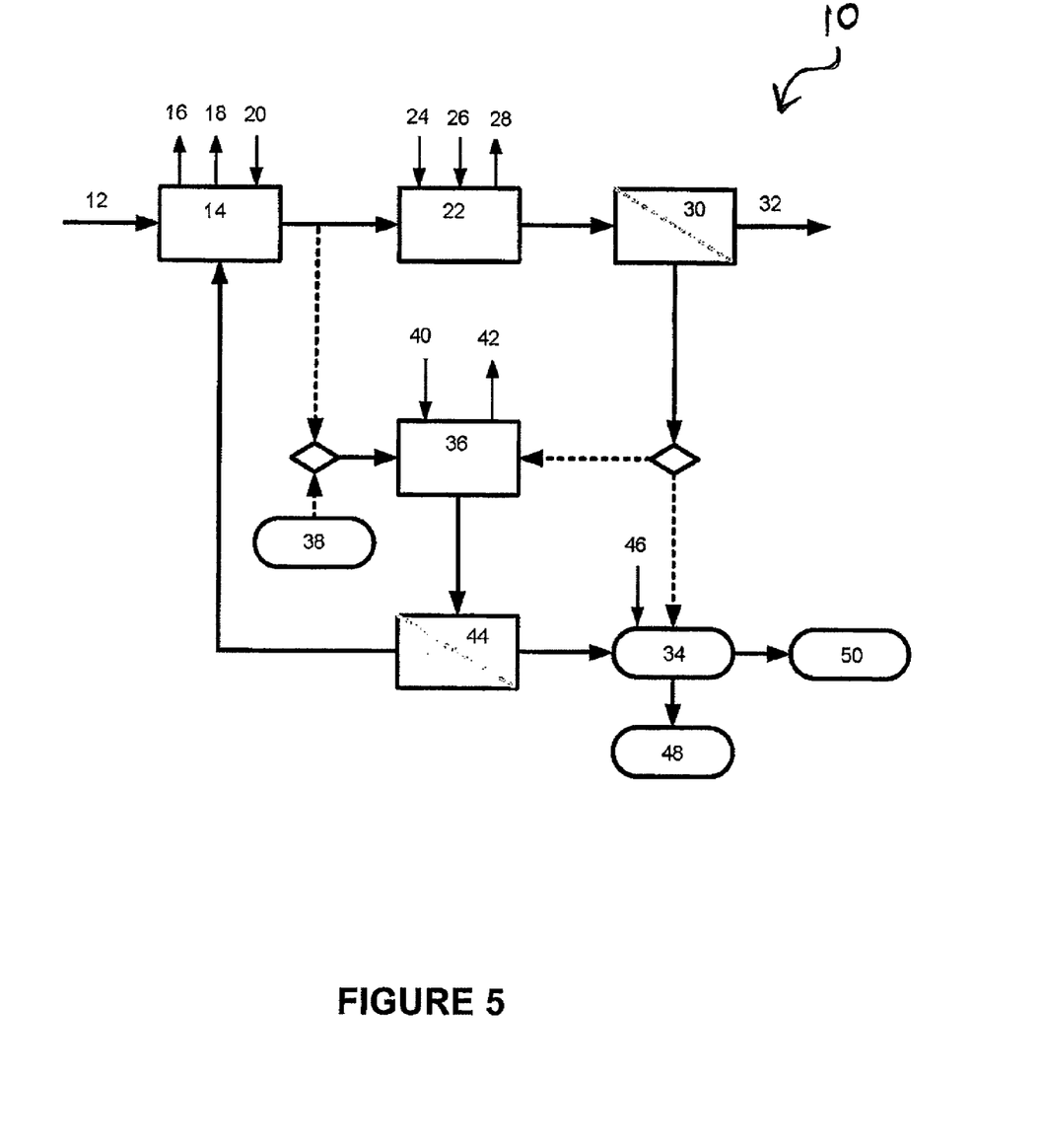
FIG. 5 is a schematic illustrating one embodiment of GAO selection process and a PHA accumulation process incorporated into a wastewater treatment system.

The GAO selection and PHA accumulation processes described above may be incorporated into a wastewater treatment system generally indicated by the numeral 10 in FIG. 5. In the embodiment illustrated herein, the wastewater treatment system may be used to treat various types of water and wastewater. The term "wastewater" as used herein means any aqueous stream that may be produced as an outlet of an industrial and/or domestic method, process or activity. In a common scenario the outlet aqueous stream contains organic and inorganic compounds that result as byproducts of the method, process or activity. In other cases however, such as for example sludge fermentation, the aqueous outlet is intended to be a volatile fatty acid rich stream and is a primary product of the method, process or activity. Thus, the term "wastewater" as used herein refers to a suitable influent to the present process and one that typically may not be directly discharged to the environment without some form of treatment.

Viewing wastewater treatment system 10 in more detail, wastewater influent 12 is directed into an Acid Phase Digester (APD) 14. During this phase of the process, organic material in the wastewater is converted into VFAs under anaerobic conditions. The organic material conversion into VFAs is allowed to proceed without permitting the further conversion of VFAs into methane and carbon dioxide. In order to control the solids retention time and pH in APD 14, biomass outlet 16 and pH adjustment inlet 20 respectively may be included in APD 14. In addition, APD 14 may include gas outlet 18. APD 14 may be a batch reactor, sequencing batch reactor, or continuous flow reactor. In addition, APD 14 may be a suspended growth reactor or biofilm growth reactor. Depending on the characteristics of the incoming wastewater influent, APD 14 may not be required. That is, if the wastewater influent is sufficiently rich in VFAs, then APD 14 may be bypassed.

After a sufficient amount of VFAs are produced in the wastewater, the wastewater is directed from APD 14 to a wastewater treatment reactor (WWT) 22. In WWT 22, organic material (dominated by VFAs) is converted into biomass and carbon dioxide. The biomass is mixed with the wastewater to form mixed liquor. The biomass is subjected to alternating anaerobic-aerobic conditions that embody the GAO selection process. In another embodiment, anoxic conditions can be used in place of or in combination with aerobic conditions. A relatively high loading ratio of VFAs to the biomass promotes an increase in glycogen levels in the GAOs. WWT 22 may be a sequencing batch reactor, a continuous flow reactor, tanks in series, a plug flow reactor, a conventional feed reactor, or a step feed reactor. WWT 22 may also include chemical addition inlets 24, aeration inlets 26, and gas outlet 28.

The wastewater containing biomass enriched in GAOs is then directed to separator 30 where the biomass is separated from treated wastewater effluent 32. In one embodiment, biomass enriched in GAOs is directed to a Downstream Processing System (DSP) 34 if the biomass has a sufficient level of PHAs. That is, if the biomass is harvested during the anaerobic phase of the GAO selection process, then the PHA content of the biomass may already be sufficient and will not need further PHA accumulation. However, if the biomass is harvested during the aerobic phase of the GAO selection process, then the biomass will have little or no PHA content. Accordingly, this type of biomass may be directed to PHA Production Process (PPP) 36 for further treatment.

In PPP 36, VFAs are added to the biomass. In one embodiment, wastewater enriched with VFAs exiting APD 14 can be directed into PPP 36. In another embodiment, an imported waste stream 38 rich in VFAs is directed into PPP 36. In yet another embodiment, both the wastewater enriched with VFAs from APD 14 and the imported waste stream 38 rich in VFAs can be directed into PPP 36. Biomass in PPP 36 is subjected to aerobic conditions, anaerobic conditions, or anaerobic-aerobic cycling. PPP 36 may be a batch reactor, a sequencing batch reactor, or a continuous flow reactor. In addition, PPP 36 may include provision for chemical addition, aeration inlets 40 and gas outlets 42.

PHA accumulation in PPP 36 is dependent on the glycogen content in the GAOs during both anaerobic and aerobic PHA accumulation. These glycogen levels can be controlled by the VFA loading in the GAO selection in the WWT 22.

After a sufficient level of PHA is produced in the GAO biomass, the biomass is directed to separator 44 where the biomass is separated from reject water. In one embodiment, the reject water may be recirculated to APD 14. The separated biomass is then directed to Downstream Processing (DSP) 34 process. DSP 34 includes any means to separate PHA from the residual biomass. This may include the addition of chemicals and mechanical energy through inlet 46 to remove non-PHA biomass from the PHA, followed by separation and drying of the PHA. The DSP 34 then separates the residual biomass, or the "non-PHA cellular material" (NCPM) 48 from PHA 50. The NCPM may be used for biogas production or may be returned to APD 14 or WWT 22.

The present invention may, of course, be carried out in other specific ways than those herein set forth without departing from the scope and the essential characteristics of the invention. The present embodiments are therefore to be construed in all aspects as illustrative and not restrictive and all changes coming within the meaning and equivalency range of the appended claims are intended to be embraced therein.

The invention claimed is:

1. A method of treating wastewater and producing polyhydroxyalkanoates (PHAs) by selecting glycogen accumulating organisms (GAOs) having a high PHA production potential in a mixed culture biomass, the method including:
    providing wastewater containing volatile fatty acids (VFAs) and a mixed culture biomass;
    selecting a GAO dominated biomass and causing the GAOs to proliferate and dominate over other microorganisms in the biomass by:
        subjecting the biomass to alternating anaerobic and aerobic or anoxic treatment, wherein the alternating anaerobic and aerobic or anoxic treatment produce the GAO dominated biomass having GAOs with relatively high levels of intracellularly stored glycogen;
        providing substantially more VFAs to the biomass during anaerobic treatment than during the aerobic or anoxic treatment such that during the anaerobic treatment, the GAOs in the GAO dominated biomass consume the VFAs and the intracellularly stored glycogen to produce PHA;
        providing the VFAs to the biomass during anaerobic treatment at a ratio of at least 0.08 g of VFA per 1 g of total suspended solids (TSS) provided; and
    accumulating the PHA in the GAO dominated biomass.

2. The method of claim 1 further comprising treatment of the wastewater under anaerobic conditions and converting the organic compounds into the VFAs through acidogenic fermentation prior to selecting a GAO dominated biomass.

3. The method of claim 1 including directing the selected biomass to a side stream PHA production zone and feeding VFAs to the biomass in the PHA production zone.

4. The method of claim 3 including subjecting the biomass in the side stream PHA production zone to aerobic conditions, anaerobic conditions, or anaerobic-aerobic or anoxic cycling.

5. The method of claim 4 including directing the biomass from the side stream PHA production zone to a separator and separating the biomass from reject water.

6. The method of claim 5 including directing the biomass separated to a downstream processing zone and separating PHA from residual biomass.

7. The method of claim 1 including harvesting the GAO dominated biomass during an aerobic or anoxic treatment phase and directing the GAO dominated biomass to a first separator and separating the GAO dominated biomass from the wastewater; and thereafter directing the GAO dominated biomass harvested to a side stream PHA production unit where VFAs are fed to the separated GAO dominated biomass.

8. The method of claim 1 wherein after the GAOs are selected VFAs are subsequently fed to the biomass so that the GAOs in the biomass consume the VFAs and produce PHA.

9. The method of claim 8 wherein the VFAs subsequently fed to the biomass are taken from a side stream prior to subjecting the biomass to alternating anaerobic and aerobic or anoxic treatment.

10. The method of claim 8 further comprising subsequently subjecting the biomass to either anaerobic, aerobic or anoxic conditions.

11. The method of claim 1 wherein the VFAs provided to the biomass while treated under anaerobic conditions is approximately 0.08 to 0.50 g of VFAs per 1 g of total suspended solids (TSS) provided.

12. The method of claim 1 wherein the biomass and wastewater are mixed to form mixed liquor and wherein subjecting the biomass to alternating anaerobic and aerobic or anoxic treatment produces the GAO dominated biomass having GAOs with at least 18% intracellularly stored glycogen under aerobic or anoxic conditions relative to the total suspended solids in the mixed liquor.

13. The method of claim 1 wherein the biomass and wastewater are mixed to form mixed liquor and wherein subjecting the biomass to alternating anaerobic and aerobic or anoxic treatment produces the GAO dominated biomass having GAOs with at least 30% intracellularly stored glycogen under aerobic or anoxic conditions relative to the TSS in the mixed liquor.

14. The method of claim 8 wherein subsequently feeding VFAs to the separated biomass produces at least 45% PHA relative to the TSS in the wastewater.

15. A method of treating wastewater and producing polyhydroxyalkanoates (PHAs) by selecting glycogen accumulating organisms (GAOs) having a high PHA production potential in a mixed culture biomass, the method including: directing wastewater containing VFAs into at least one wastewater treatment zone containing a mixed culture biomass; selecting a GAO dominated biomass and causing the GAOs to proliferate and dominate over other microorganisms in the biomass in the wastewater treatment zone by: subjecting the biomass to alternating anaerobic and aerobic or anoxic treatment in the wastewater treatment zone(s), wherein the alternating anaerobic and aerobic or anoxic treatment produces the GAO dominated biomass having GAOs with relatively high levels of intracellularly stored glycogen; providing substantially more VFAs to the biomass during anaerobic treatment than during aerobic or anoxic treatment such that during the anaerobic treatment, the GAOs in the GAO dominated biomass consume VFAs and the intracellularly stored glycogen to produce PHA; providing the VFAs to the biomass during anaerobic treatment at a ratio of at least 0.08 g of VFA per 1 g of total suspended solids (TSS) provided to the anaerobic treatment; and adding VFAs to the GAO dominated biomass in a PHA production zone such that the GAOs consume VFAs and produce PHA.

16. The method of claim 15 further comprising treating the wastewater under anaerobic conditions and converting the organic compounds into the VFAs through acidogenic fermentation prior to selecting the GAO dominated biomass.

17. The method of claim 15 wherein the VFAs added to the GAO dominated biomass in the PHA production zone are taken from the wastewater prior to subjecting the biomass to alternating anaerobic and aerobic or anoxic treatment.

18. The method of claim 15 further comprising subjecting the biomass to anaerobic, aerobic or anoxic conditions in the PHA production zone.

19. The method of claim 15 wherein selecting the GAO dominated biomass occurs in a main stream and wherein the PHA production zone is disposed in a side stream.

20. The method of claim 15 including selecting the GAO dominated biomass in a main stream and separating the biomass from the wastewater and directing the separated biomass to a PHA production zone located in a side stream.

21. A method of biologically treating wastewater in a mixed culture biomass and producing polyhydroxyalkanoates (PHAs) in the biomass by selecting glycogen accumulating organisms (GAOs) having a high polyhydroxyalkanoates (PHAs) production potential, the method comprising:
directing wastewater influent into at least one reactor and biologically treating the wastewater with the biomass;
implementing a GAO selection process by selecting GAOs in the biomass and causing the GAOs to proliferate and dominate over non-GAOs in the biomass;
the GAO selection process including:
subjecting the biomass to alternating anaerobic and aerobic or anoxic conditions by subjecting the biomass to alternating anaerobic and aerobic or anoxic treatment phases;
providing more feed in the form of VFAs to the biomass during the anaerobic treatment phase than during the aerobic or anoxic treatment phase;
subjecting the biomass to the alternating anaerobic and aerobic or anoxic treatment phases resulting in a GAO dominated biomass having GAOs with substantial levels of intracellular stored glycogen, and wherein the GAOs in the GAO dominated biomass consumed the VFAs and the intracellular stored glycogen to produce PHAs;
providing the VFAs to the biomass during anaerobic treatment at a ratio of at least 0.08 g of VFA per 1 g of total suspended solids (TSS) provided to the anaerobic treatment; and accumulating PHA in the GAO dominated biomass.

22. The method of claim 21 including separating the PHA in the GAO dominated biomass from the wastewater and accumulating or harvesting PHA from the GAO dominated biomass.

23. The method of claim 21 wherein accumulating the PHA in the GAO dominated biomass includes feeding VFAs to the biomass and converting the VFAs to PHA.

24. The method of claim 21 wherein the influent wastewater includes substantial VFAs or the method includes converting organic matter in the influent wastewater to VFAs such that VFAs are made available to the biomass during the anaerobic treatment phases, and wherein during the anaerobic treatment phases the method entails providing relatively high VFA loading compared to the VFA loading during the aerobic or anoxic treatment phases.

25. The method of claim 21 wherein the selection of GAOs is carried out in a sequencing batch reactor and the VFAs to biomass ratio is at least approximately 0.08 g-VFA/g-TSS where the ratio is defined as the mass of VFAs fed to the biomass during the anaerobic treatment phases divided by the mass of the biomass, measured at approximately the start of the anaerobic phases.

26. The method of claim 21 wherein biologically treating the wastewater with the biomass includes removing biochemical oxygen demand (BOD) from the wastewater.

27. The method of claim 21 wherein the biomass is mixed with the wastewater to form mixed liquor and the method includes controlling the selection of GAOs by controlling: (1) the ratio of the amount of VFAs fed with the wastewater compared to the amount of biomass in the mixed liquor; (2) the retention time of the biomass during anaerobic and aerobic or anoxic treatment; (3) the temperature of the wastewater during anaerobic and aerobic or anoxic treatment; (4) the ratio of phosphorus to carbon source provided; or (5) any combination thereof.

28. The method of claim 21 further including harvesting PHA from the GAO dominated biomass after the biomass has been subjected to anaerobic treatment without any substantial intervening aerobic or anoxic treatment by directing the GAO dominated biomass to a first separator and separating the biomass from the wastewater; and directing the GAO dominated biomass to a downstream processing unit and separating PHA from residual biomass.

29. The method of claim 21 including harvesting the GAO dominated biomass during an aerobic or anoxic treatment phase and directing the GAO dominated biomass to a first separator and separating the GAO dominated biomass from the wastewater; thereafter directing the GAO dominated biomass harvested to a side stream PHA production unit where VFAs are fed to the separated GAO dominated biomass.

30. The method of claim 29 wherein after the biomass has been subjected to the side stream PHA production process, directing the GAO dominated biomass to a second separator and separating PHA from residual biomass.

* * * * *